(12) United States Patent  (10) Patent No.: US 8,828,711 B2
Jaron et al.  (45) Date of Patent: Sep. 9, 2014

(54) FLOW CHAMBER AND ANALYTE DETECTION METHOD

(75) Inventors: Dov Jaron, Philadelphia, PA (US); Kenneth A. Barbee, Philadelphia, PA (US); Allison M. Andrews, King of Prussia, PA (US)

(73) Assignee: Drexel University, Philadelphia, PA (US)

( * ) Notice: Subject to any disclaimer, the term of this patent is extended or adjusted under 35 U.S.C. 154(b) by 128 days.

(21) Appl. No.: 13/117,473

(22) Filed: May 27, 2011

(65) Prior Publication Data

US 2011/0294154 A1   Dec. 1, 2011

Related U.S. Application Data

(60) Provisional application No. 61/349,533, filed on May 28, 2010.

(51) Int. Cl.
*C12M 1/34* (2006.01)
*G01N 33/53* (2006.01)

(52) U.S. Cl.
CPC .................................. *G01N 33/5302* (2013.01)
USPC .................. 435/286.5; 435/287.1; 435/297.2; 435/29

(58) Field of Classification Search
USPC ...................................................... 435/287.1
See application file for complete search history.

(56) References Cited

U.S. PATENT DOCUMENTS

| | | | |
|---|---|---|---|
| 3,998,717 A * | 12/1976 | Watson et al. | 204/403.1 |
| 4,620,918 A * | 11/1986 | Bukamier et al. | 204/403.02 |
| 5,160,604 A * | 11/1992 | Nakamura et al. | 204/403.06 |
| 5,356,792 A | 10/1994 | Maeda et al. | |
| 6,562,616 B1 | 5/2003 | Toner et al. | |
| 6,706,160 B2 | 3/2004 | Kriz | |
| 2006/0154361 A1 * | 7/2006 | Wikswo et al. | 435/289.1 |

OTHER PUBLICATIONS

Andrews, et al, "An Innovation Device for the Real-Time, Direct Measurement of Shear-Stress Induced Nitric Oxide (NO) Production from Endothelial Cells In Vitro", Third International Meeting on the Role of Nitrite in Physiology, Pathophysiology, and Therapeutics, Stockholm, Sweden, 2009 Source: Nitrite Oxide 20 (2009) S29-S48.
Andrews, et al, Direct, Real-Time Measurement of Shear-Stress Induced Nitric Oxide Production from Endothelial Cells In Vitro, Abstract at oral presentation—that was not published in journal, only in program booklet.
Brooks, et al, "Concentration Dependent Effcts of Nitrite Oxide on Mitochondrial Permeability Transition and Cytochrome c Release", J. Biol. Chem 275, 20474-9 (2000).
Dailey, et al, "Culture Chambers for Live-Cell Imaging" Mar. 21, 2009.
FCS2 Closed Chamber Syatem, Apr. 10, 2009.

(Continued)

*Primary Examiner* — William H Beisner
(74) *Attorney, Agent, or Firm* — Mendelsohn, Drucker & Dunleavy, P.C.

(57) ABSTRACT

A flow chamber and method for detecting the presence of one more cell produced analytes under flow conditions. The flow chamber includes two compartments separated by a permeable membrane on which a plurality of cells may be positioned. The permeable membrane shields one or more analyte sensors positioned one compartment from the convective transport forces of a fluid flow within the other compartment to allow reliable and accurate detection of cell-produced analytes and determination of the concentration of cell-produced analytes.

20 Claims, 10 Drawing Sheets

(56) References Cited

OTHER PUBLICATIONS

Hastings, et al, Atherosclerosis-prone Hemodynamics Differentially Regulates Endothelial and Smooth Muscle Cell Phenotypes and Promotes Pro-inflammatory Priming, Am J Physiol Cell Physiol 293:1824-1833, 2007. First published Oct. 3, 2007; doi:10.1152/ajpcell.00385.2007.
Nitrite Oxide, 20 (2009) S29-S48, Poster Abstracts.
Kemeny, et al, Glycated Collagen Alters Endothelial Cell Act in Alignment and Nitric Oxide Release in response to Fluid Shear Stress.
Dual Chamber Oxygen Measuring System.
Article, Nitric Oxide 23 (2010) 335-342.
G.M. Buga, M.E. Gold, J.M. Fukuto, and L.J. Ignarro, Shear-stress induced release of nitricoxide from endothelial-cells grown on beads. Hypertension 17 (1991) 187-193.
M.J. Kuchan, and J.A. Frangos, Role of calcium and calmodulin in flow-induced nitric-oxide production in endothelial-cells. American Journal of Physiology 266 (1994) C628-C636.
M.A. Corson, N.L. James, S.E. Latta, R.M. Nerem, B.C. Berk, and D.G. Harrison, Phosphorylation of endothelial nitric oxide synthase in response to fluid shear stress. Circulation Research 79 (1996) 984-991.
W.P. Qiu, D.A. Kass, Q.H. Hu, R.C. Ziegelstein, Determinants of shear stress-stimulated endothelial nitric oxide production assessed in real-time by 4,5-diaminofluorescein fluorescence, Biochem. Biophys. Res. Commun. 286 (2001) 328-355.
X.Y. Ye, S.S. Rubakhin, and J.V. Sweedler, Detection of nitric oxide in single cells. Analyst 133 (2008) 423-433.
N. Vukosavljevic, D. Jaron, K.A. Barbee, and D.G. Buerk, Quantifying the L-arginine paradox in vivo. Microvascular Research 71 (2006) 48-54.
F. Palm, D.G. Buerk, P.O. Carlsson, P. Hansell, and P. Liss, Reduced nitric oxide concentration in the renal cortex of streptozotocin-induced diabetic rats—Effects on renal oxygenation and microcirculation. Diabetes 54 (2005) 3282-3287.
S. Mochizuki, M. Goto, Y. Chiba, Y. Ogasawara, and F. Kajiya, Flow dependence and time constant of the change in nitric oxide concentration measured in the vascular media. Med Biol Eng Comput 37 (1999) 497-503.
A.A. Fadel, K.A. Barbee, and D. Jaron, A computational model of nitric oxide production and transport in a parallel plate flow chamber. Annals of biomedical engineering 37 (2009) 943-954.
Suthan Srigunapalan et al, A microfluidic membrane device to mimic critical components of the vascular microenvironment.
Nicholas Ferrell, et al, A Microfluidic Bioreactor With IntegratedTransepithelial Electrical Resistance (TEER) Measurement Electrodes for Evaluation of Renal Epithelial Cells, Biotechnol. Bioeng. 2010;107: 707-716.
Andrews et al, Measurement of real-time direct shear-stress induced nitric oxide production from endothelial cells in vitro, Abstract.

* cited by examiner

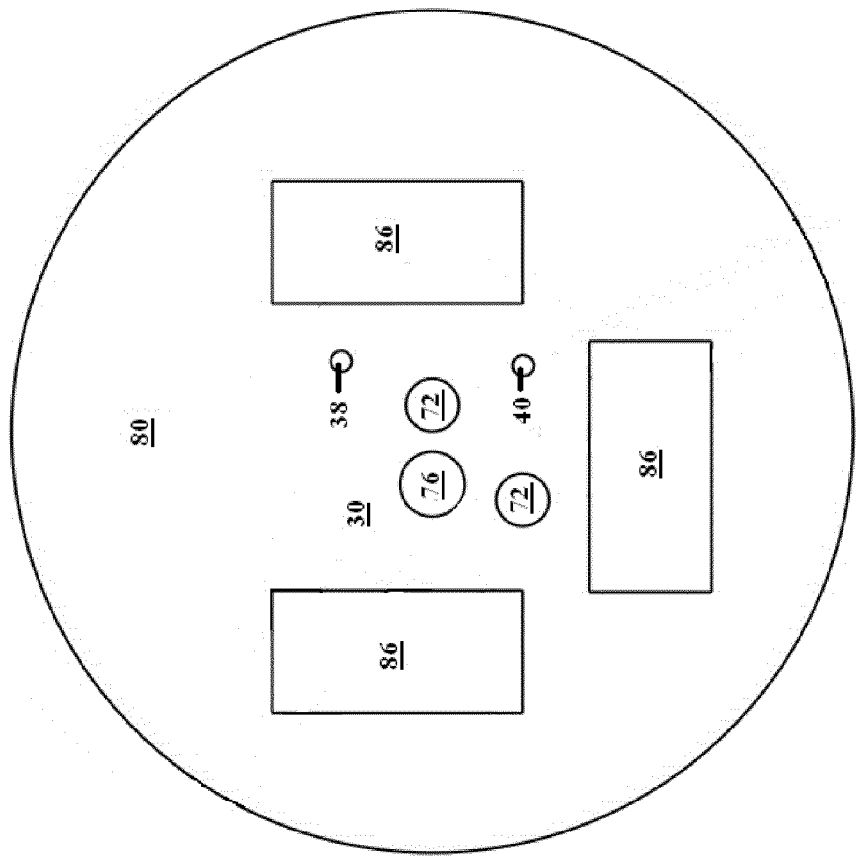
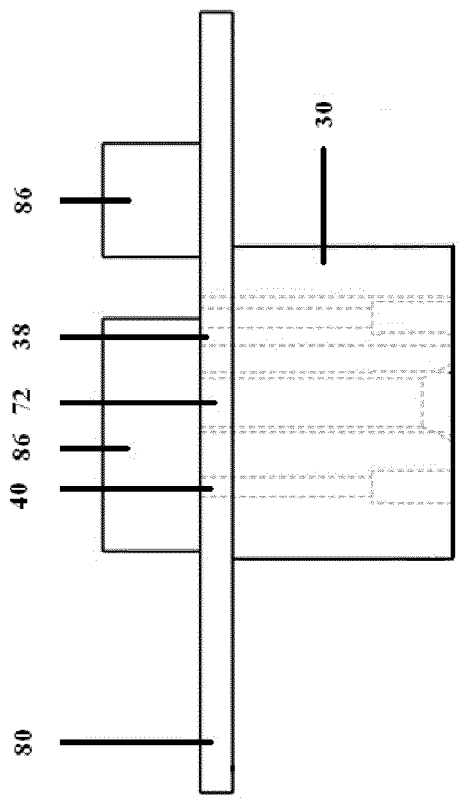
FIGURE 2
FIGURE 3

FLOW CHAMBER AND ANALYTE DETECTION METHOD

STATEMENT OF GOVERNMENT INTEREST

This invention was reduced to practice with Government support under Grant No. NIH/HL068164 awarded by the National Institutes of Health and Grant No. NSF/BES0301446 awarded by the National Science Foundation; the Government is therefore entitled to certain rights to this invention.

BACKGROUND OF THE INVENTION

1. Field of the Invention

The invention relates to a flow chamber and a method for detecting low concentrations of molecules produced by cells.

2. Description of the Related Technology

The flow conditions in conventional single compartment flow chambers present difficulties in detecting and measuring cell-produced diffusible molecules, which are typically produced in low concentrations. Diffusible molecules are rapidly carried from the cell surface into the flow current due to convective transport, forming a steep concentration gradient that inhibits the accurate measurement of the diffused molecule concentration. The sensors utilized in conventional flow chambers are also typically unable to make accurate measurements under flow conditions due to the sensor placement and poor flow signal sensitivity. Consequently, single compartment flow chambers are unable to accurately or reliably detect or measure the amount of diffusible molecules produced by cells contained within the single compartment flow chamber.

Specifically, conventional flow chamber systems are incapable of accurately detecting and measuring cell nitric oxide (NO) generated by cells placed under shear stress by contact with a flowing fluid. NO is known to rapidly diffuse and has a short half-life of about 2-30 seconds. Consequently, NO produces sharp gradients in concentration near the source of production due to convective transport which rapidly removes the NO that diffuses into the fluid from the cell surface. The steep concentration gradient and low concentration levels of NO produced by cells make accurate and reliable NO measurements under controlled in vitro conditions virtually impossible. Although, placement of the NO sensing electrodes close to the exposed cell surface can reduce the potential effects discussed above, such an electrode placement will cause disturbances in the flow profile in the vicinity of the cells being monitored thereby altering the results by changing the effective shear stress due to the flow on some or all of the cells. Furthermore, the electrodes used for NO measurement, can also be sensitive to flow, thereby further distorting or masking the NO signal.

Research on shear stress-induced NO production has been severely limited because of the foregoing experimental difficulties and detection limitations on concentration and accuracy. NO detection measured in a system which applies changes in shear stress by changing the fluid flow is particularly challenging because of the low NO concentrations and the many competing phenomena including convection, diffusion, and chemical degradation. Similar problems exist in relation to measurement of other cell-generated species as well.

Consequently, there is a need to develop an improved flow chamber that addresses the deficiencies of the prior art and enables detection and measurement of low concentration cell produced diffusible molecules, such as NO.

SUMMARY OF THE INVENTION

In a first aspect, the invention is directed to a flow chamber for detecting an analyte. The flow chamber includes a first compartment having a fluid inlet and fluid outlet for allowing a fluid to flow through the first compartment. The flow chamber further includes a second compartment and an analyte sensor positioned within the second compartment. A permeable membrane, having a first surface that is exposed to fluid flow in the first compartment a second surface positioned within the second compartment separates the first and second compartments.

In a second aspect, the invention is directed to a flow chamber for detecting an analyte. The flow chamber includes a first compartment having a fluid inlet and fluid outlet for allowing a fluid to flow through the first compartment. The flow chamber further includes a second compartment and an analyte sensor positioned within the second compartment. The flow chamber also includes a structure for allowing passage of an analyte from the first compartment to the second compartment, wherein the analyte sensor is positioned at a known distance from a surface of said structure.

In a third aspect, the invention is directed to a method for detecting an analyte using a flow chamber described in the first aspect of the invention. The method involves positioning a plurality of cells within the flow chamber on the first surface of the permeable membrane. The analyte sensor may be positioned a known distance from said plurality of cells. Fluid is flowed through the first compartment, and the analyte produced by said plurality of cells is detected.

BRIEF DESCRIPTION OF THE DRAWINGS

FIG. 2 is a bottom view of a sensor holder for retaining an analyte sensor in a sensing position without the sensors present.

FIG. 3 is a side view of the sensor holder of FIG. 2.

FIG. 8(b) is a graph the time constant as a function of shear stress change for experiments involving a change in shear stress from 0.1 dyn/cm$^2$ to 1, 6, 10 and 20 dyn/cm$^2$a.

DETAILED DESCRIPTION OF THE PREFERRED EMBODIMENTS

Figure 1:
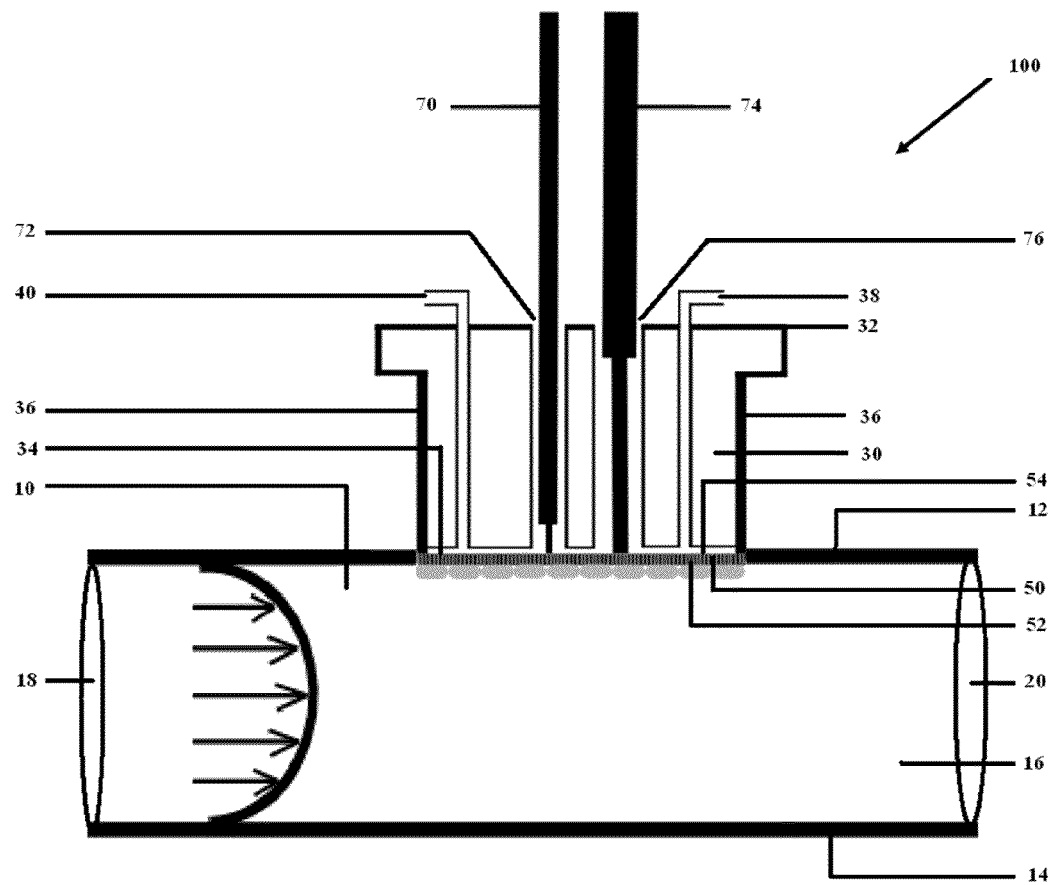
FIG. 1 is a cross-sectional view of an exemplary flow chamber in accordance with the present invention with the sensors located in the chamber.

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

It must be noted that as used herein and in the appended claims, the singular forms "a", "an", and "the" include plural references unless the context clearly dictates otherwise. Additionally, the terms "a" (or "an"), "one or more" and "at least one" can be used interchangeably herein. It is also to be noted that the terms "comprising", "including", and "having" can be used interchangeably.

The present invention is directed to a flow chamber 100 and method for detecting the presence of one more cell-produced analytes under flow conditions. Flow chamber 100 includes a first compartment 10 and a second compartment 30 separated by a permeable membrane 50 on which a plurality of cells may be positioned. Permeable membrane 50 serves to insulate one or more analyte sensors 70 positioned within second compartment 30 from the convective transport forces of fluid flow within second compartment 30. Analyte sensor 70, located proximate to permeable membrane 50, enables the detection of one or more cell-produced analytes that diffuse through permeable membrane 50. Cell-produced analytes are generated in response to an applied stimulus and diffuse through permeable membrane 50 into second compartment 30 where the analytes are detected by analyte sensor 70. In an exemplary embodiment, the invention enables the determination of analyte concentration or a change in analyte concentration over time.

As shown in FIG. 1, flow chamber 100 includes two compartments 10, 30 and is arranged to detect the presence of one or more cell-produced analytes generated in response to an applied stimulus. A first compartment 10 is configured as an enclosed structure defined by a ceiling 12, floor 14 and plurality of side walls 16. First compartment 10 further includes a fluid inlet port 18 and fluid outlet port 20 through which a fluid may be flowed, for example, in order to apply shear stress to cells positioned therein. In one embodiment, a fluid source is connected to fluid inlet 18 via a conduit and supplies a fluid to first compartment. The fluid is subsequently expelled via fluid outlet port 20 and drained from the substantially closed system. Alternatively, fluid inlet port 18 and fluid outlet port 20 may be connected via a conduit, forming a substantially closed system wherein a fluid may be continuously circulated. In an exemplary embodiment, first compartment 10 forms a substantially controlled and closed system, wherein a pump is attached to and/or valves are positioned within fluid inlet port 18, fluid out let port 20, one or more conduits connected thereto or combinations thereof in order to set and regulate the pressure within and prevent leakage of fluid from first compartment 10.

A second compartment 30 formed as a substantially enclosed or enclosed interior space defined by a ceiling 32, floor 34 and plurality of side walls 36, may be configured as a closed system. In an exemplary embodiment, second compartment 30 forms a substantially small, enclosed space in order to ensure that the contents of second compartment 30 and the diffused analyte quickly achieve equilibrium. In an exemplary embodiment, second compartment 30 has a volume of about 1000 ml or less, preferably, about 500 µL to about 800 µL. Second compartment 30 is located proximate to a permeable membrane 50 separating first and second compartments 10, 30. Due in part to the small volume and zero flux condition at the other boundaries of second compartment 30 and the short diffusion distance from permeable membrane 50, the concentration of an analyte in second compartment 30 is substantially uniform and rapidly equilibrates with the analyte concentration in the cell layer. Optionally, second compartment 30 may include a fluid inlet port 38 and fluid outlet port 40 that allows for a fluid to be introduced, contained and/or flowed through second compartment 30 for the purpose of rinsing second compartment 30 and its contents. In an exemplary embodiment, second compartment 30 may have the same flow system components and system configuration as that of first compartment 10.

Separating two or more compartments of flow chamber 100 is a permeable membrane 50, which may be configured as any porous substrate that provides a surface on which a plurality of cells may be positioned. In the embodiment of FIG. 1, a plurality of cells are immobilized and/or cultured on a first surface 52 of permeable membrane 50 that is exposed to fluid flow within first compartment 10. For purposes of the present invention, any group of cells may be positioned on first surface 52 of permeable membrane 50, forming one or more cellular layers or a tissue matrix. Exemplary cells include cells that can adhere to or be cultured on a two dimensional substrate, such as epithelial cells, endothelial cells, vascular smooth muscle, fibroblasts, osteoblasts, chondrocytes, endothelial cells, including lymphatic endothelial cells, and stem cells at various stages of differentiation.

Permeable membrane 50 allows for the passage of at least one analyte of interest from first compartment 10 to second compartment 30, particularly analytes produced by the cells positioned on permeable membrane 50. Exemplary analytes include small molecules, preferably dissolved gases, such as nitric oxide (NO) and oxygen; ions such as calcium, potassium, magnesium, hydrogen (pH); sugars, such as glucose, nucleotides such as adenosine triphosphate (ATP), adenosine diphosphate (ADP), and adenosine monophosphate (AMP); small proteins, such as endothelin; and lipids such as prostacyclin. Large molecule analytes, however, may also be investigated using flow chamber 100. In an exemplary embodiment, permeable membrane 50 has a plurality of apertures or pores that allow for the diffusion of small analytes through permeable membrane 50. In an exemplary embodiment, the size of each aperture or pore is from about 0.1 µm to about 12 µm in diameter, preferably, from about 0.1 µm to about 8 µm in diameter, more preferably, from about 0.4 µm to about 5 µm in diameter and most preferably, from about 0.4 µm to about 3 µm in diameter. Additionally, the porosity, i.e. area fraction of the pores, of permeable membrane 50 may be up to about 0.14, preferably, up to about 0.005 and more preferably, from about 0.005 to about 0.5. The selected pore size and porosity of permeable membrane 50 is dependent upon the diffusibility of the analyte being investigated.

Positioned between first and second compartments 10, 30, permeable membrane 50 is designed to shield the contents and environment of second compartment 30 from the convective forces generated by fluid flow in first compartment 10. Specifically, the structure of permeable membrane 50 substantially shields the cell-produced analytes that have diffused across permeable membrane 50, analyte sensor 70 and any fluid contained within first compartment 10 from the convective fluid flow within first compartment 10. This shielding effect is achieved by virtue of the fact that permeable membrane 50 forms a structural barrier that substantially inhibits the fluid flow, and consequently substantially inhibits or prevents the kinetic transfer of flow force, between the first and second compartments 10, 30.

As shown in the embodiment of FIG. 1, permeable membrane 50 separates and forms a structural barrier between the first and second compartments 10, 30. First surface 52 of permeable membrane 50 forms first compartment ceiling 12 and second surface 54 of permeable membrane 50 forms second compartment floor 34. Permeable membrane 50 is preferably positioned flush with respect to a wall of first compartment 10, allowing for a laminar and uniform fluid flow in first compartment 10. Alternatively, permeable membrane 50 may be positioned so as to protrude or be recessed within first compartment 10, thereby causing a more complex and possibly turbulent fluid flow pattern in first compartment 10 due to interference of the permeable membrane 50 with the fluid flow. As shown in FIG. 1, permeable membrane 50 is arranged so as to separate flow chamber 100 into a first compartment 10 and a second compartment 30. One of ordinary skill in the art, however, would appreciate that so long as permeable membrane 50 creates a structural barrier between two or more compartments of flow chamber 100, alternative flow chamber configurations may be utilized. For example, first and second compartments 10, 30 may be arranged in a side-by-side orientation, wherein permeable membrane 50 forms side walls 16, 36 of first and second compartments 10, 30.

One or more analyte sensors 70, positioned within second compartment 30, can be used to detect the presence of an analyte, determine analyte concentration, determine a change in analyte concentration, determine analyte production rate or combinations thereof. In one embodiment, two or more analyte sensors 70 may be positioned within second compartment 30, wherein each analyte sensor 70 is customized to detect a different analyte. Alternatively, a plurality of the same analyte sensors 70 can be positioned at different locations within second compartment 30. This embodiment may be useful, for example, for studying the effects of complex flow patterns on the generation of analytes by cells since it could give information about analyte generation at different locations along the immobilized cells exposed to a stimulus, such as a fluid flow in first compartment 10. Analyte sensor 70 may be any sensor suitable for detecting an analyte, such as an electrode or piezoelectric cantilever sensor, and may be capable of detecting an analyte under dry or wet environmental medium. Exemplary analyte sensors 70 may include high sensitivity sensors capable of detecting small molecules, preferably dissolved gases, such as nitric oxide (NO) and oxygen; ions such as calcium, potassium, magnesium, hydrogen (pH); sugars, such as glucose, nucleotides such as ATP, ADP, and AMP; small proteins, such as endothelin; and lipids such as prostacyclin.

In order to quantify the concentration or change in concentration of one or more analytes produced by the cells positioned on permeable membrane 50, analyte sensor 70 may be placed within second compartment 30 at a known, fixed distance from the cells, which can be approximated by the distance to first surface 52 of permeable membrane 50. Alternatively, second compartment 30 can be fabricated to be sufficiently small that fluid contained in second compartment 30 will quickly equilibrate with cell-generated analyte that diffuses through permeable membrane 50 to provide quantitative information about analyte concentration. Analyte sensor 70 may be fixed to, or located proximate to, any surface of second compartment 30, including ceiling 12, floor 14, side walls 16, or combinations thereof. Alternatively, analyte sensor 70 may be removably inserted into second compartment 30 via an analyte sensor port 72. The distance between analyte sensor 70 and the cell surface/first exposed surface 52 maybe adjusted and fixed by virtue of fasteners, such as clamps and threaded fasteners. In an exemplary embodiment, second compartment 30 may be constructed from a substantially transparent material having a plurality of graduated indicators on a surface thereof that provides a guide and means for measuring the distance between analyte sensor 70 and first surface 52 of membrane 50 on which the cells are located.

Figure 4:
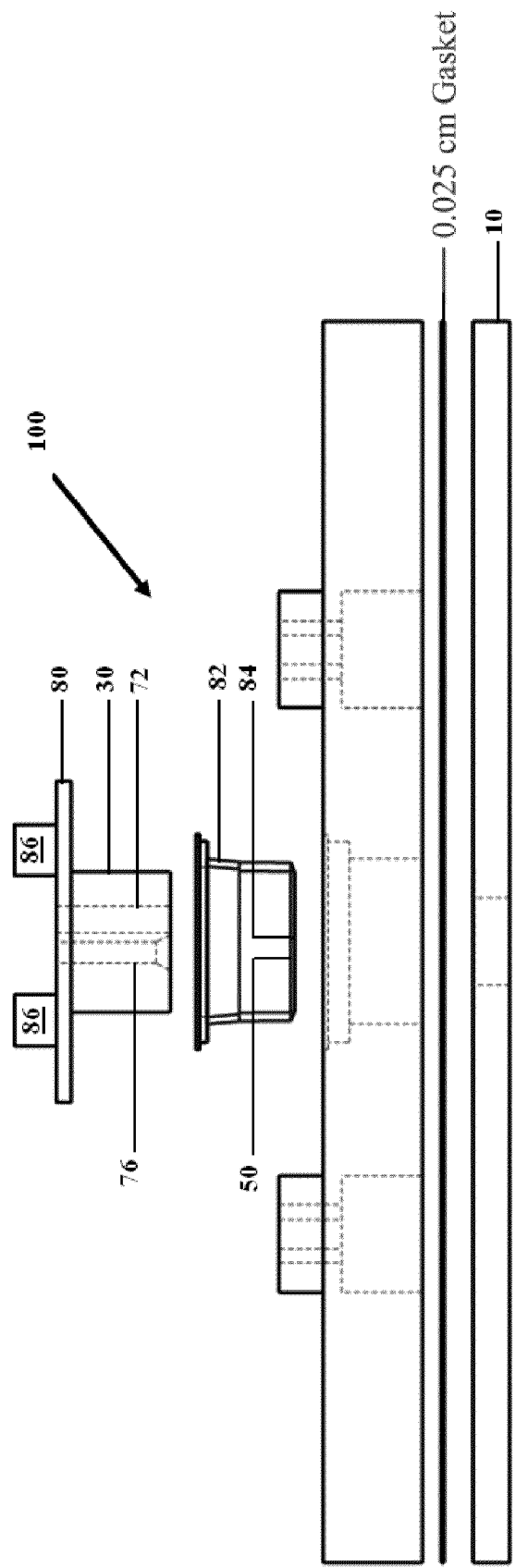
FIG. 4 is an exploded view of a parallel plate flow chamber including a sensor holder without the sensors present.

In the embodiments shown in FIGS. 2-4, flow chamber 100 further includes a sensor holder 80 that can be associated with second compartment 30 and analyte sensors 70 to facilitate positioning analyte sensors 70 in a fixed, predetermined distance relative to the first surface 52 of permeable membrane 50. Sensor holder 80, having the interior space defining and second compartment 30, is inserted into a sleeve 82 configured as a container with a shape, size and dimensions that corresponds to and is adapted to securely receive a portion of sensor holder 80, preferably the interior space defining second compartment 30 and second compartment 30. In this embodiment, permeable membrane 50 forms a lower surface 84 of sleeve 82. Preferably, the distance between a lower surface of sensor holder 80 and permeable membrane 50 is about 300 µm. Sleeve 82 is adapted to contain one or more liquids, providing a sensing medium in which analyte sensor 70 is bathed upon insertion into sleeve 82. Prior to insertion into sleeve 82, floor 34 is absent from second compartment 30, creating an open system wherein a distal end of sensor 70 is unconfined. Optionally, one or more micromanipulators 86 may be attached to sensor holder 80 in order to allow a user to interact with sensor holder 80, second compartment 30, analyte sensor 70 or a combination thereof when flow chamber 100 is placed under a microscope.

To facilitate the detection of analytes present in low concentration, analyte sensors 70 can be positioned proximate to second surface 52 of permeable membrane 50. Preferably, analyte sensor 70 may directly contact second surface 52 of permeable membrane. In an exemplary embodiment, analyte sensor 70 is positioned about 5 μm to about 50 μm, preferably, about 5 μm to about 20 μm, from a second surface 52 of membrane 50. The selected distance of analyte sensor 70 relative to exposed surface 52 may be dependent upon the size and concentration of the analyte being investigated. The purpose of accurately positioning the analyte sensor 70 is that it allows calculation of analyte concentrations from known concentration gradients in case it is desirable to determine analyte concentrations in this manner.

In addition to analyte sensors 70, flow chamber 100 may include one or more environmental sensors 74 for monitoring one or more environmental conditions of one or more compartments of flow chamber 100. Exemplary environmental sensors 74 that may be positioned within first or second compartment 10, 30 may include temperature sensors, pressure sensors, flow rate sensors or combinations thereof. Environmental sensors 74 may be fixed to a surface of, or removably inserted via an environmental sensor port 76 into, a flow chamber compartment 10, 30. In an exemplary embodiment, environmental sensors 74 may be connected to a system capable of adjusting an environmental condition of a flow chamber compartment in response to measurements obtained from one or more environmental sensors 74.

During operation, a plurality of cells may be immobilized and/or cultured on first surface 52 of permeable membrane 50. While a plurality of cells may be positioned on first surface 52 forming multiple cell layers that extend into the interior of first compartment 10, the cells adjacent to the first surface 52 of membrane 50 are located at a known distance relative to analyte sensor 70 since this distance can be determined by summing the thickness of membrane 50 with the distance from analyte sensor 50 to second surface 54 of membrane 50. Specifically, as shown in FIG. 1, the cells directly contact and are aligned along first surface 52. Consequently, the distance between sensor 70 and the plurality of cells may be approximated by the distance between sensor 70 and first surface 52.

A stimulus is then applied to the cells, inducing the cells to generate or change the production of one or more analytes. In an exemplary embodiment, the applied stimulus may be shear stress exerted on the cells by a fluid flow within first compartment 10; the addition or withdrawal of stimulating or inhibiting molecules under steady fluid flow conditions in first compartment 10; environmental changes, such as changes in temperature, pressure or flow rate, in first compartment 10; or combinations thereof.

In one embodiment, a fluid is flowed through first compartment 10 in a direction substantially parallel to ceiling 12, forming a laminar flow that applies a substantially uniform shear stress to the cells. The applied shear stress induces the cells to produce or modify the production of one or more analytes. In an exemplary embodiment, the physiological shear stress applied to the cells is about 0 to about 200 dyn/cm$^2$. It is desirable to achieve the shear stress with the lowest flow rates possible in order to limit the convective transport of the analyte. This may be accomplished by minimizing the cross-sectional dimensions of the flow chamber subject to practical limitations and desired uniformity of the flow field.

Alternatively, the fluid flow may have a more complex and/or turbulent flow pattern that may be achieved using a variety of different methods. In one embodiment, a complex flow pattern may be created by virtue of the placement of permeable membrane 50 relative to the fluid flow. In another embodiment, the geometry of flow chamber 100 or one or more components thereof can be configured or modified so as to produce any number of flow patterns of interest. For example, a sudden expansion in first compartment 10 would produce flow separation creating a recirculation zone that mimics flow at branch points in blood vessels. Also, the flow pattern may be modified by fluctuation of the fluid flow rate. In addition to incremental step changes in flow rate, any number of time-dependent flow patterns including periodic waveforms could be used.

The cell-produced analytes that are generated in response to the stimulated cells diffuse through permeable membrane 50 into second compartment 30. By virtue of the small, substantially closed and stagnant fluid environment, of second compartment 30, the fluid and analyte within second compartment 30 can be induced to quickly reach equilibrium. Additionally, permeable membrane 50 provides a structural barrier that insulates the diffused analytes from the effect of convective transport due to fluid flow in first compartment 10, ensuring that the measurements made by one or more analyte sensors 70 positioned within second compartment 30 accurately reflect the analyte concentration produced by the cells. These features enable flow chamber 100 to accurately and reliably detect and/or measure the concentration of analytes present in low concentrations.

In order to quantify analyte concentration without having to allow the contents of second compartment 30 to equilibrate and/or detect a change in analyte concentration over time within second compartment 30, analyte sensor 70 may be fixed or removably positioned within second compartment 30 at a known distance relative to the first surface 52 of membrane 50 on which the cells are located. Preferably, a distal end of analyte sensor 70 contacts second surface 54 of membrane 50 to establish a distance between distal end of analyte sensor 70 and first surface 52 of membrane 50 equal to the membrane thickness.

In the embodiment shown in FIGS. 2-4, second compartment 30 and analyte sensor 70 may be attached to a sensor holder 80 and bathed within a liquid bath contained within sleeve 82 to enhance detection sensitivity. Sensor holder 80, which has an interior space defining second compartment 30, is subsequently inserted into sleeve 82, containing a fluid bath in which analyte sensor 10 is bathed. Flow cell 100 may be placed on the platform of a microscope and sensor holder 80, second compartment 30, analyte sensor 70, or combinations thereof may be manipulated using micromanipulators 86.

Upon fixing the distance between sensor 70 and first surface 52 of membrane 50, it may be possible to determine the change in analyte concentration over a predetermined interval of time by comparing measurements taken by analyte sensor 70 at two different predetermined flow rates or by employing more complicated flow patterns which, for example, vary over time. Analyte concentration within second compartment 30 may also be determined at a predetermined point by calibrating analyte sensor 70, for example, by flushing second compartment 30 with an experimental fluid to obtain a baseline value for a particular analyte.

To calibrate sensor 70 and enhance the accuracy of the measurements taken by sensor 70, second compartment 30 and analyte sensor 70 positioned therein may be periodically rinsed by flushing a liquid, such as distilled water or cleaning solution, through second compartment 30, said fluid entering via inlet port 38 and exiting at outlet port 40. Additionally, analyte sensor 70 may be periodically removed from flow chamber 100 for cleaning between measurements.

To further ensure optimal sensing conditions, environmental sensors 74 may be positioned within first and/or second compartment 10, 30 to monitor an environmental condition of the compartment, such as pressure, temperature and fluid flow rate. A system, operatively associated with environmental sensors 74, may automatically adjust and regulate one or more environmental conditions of the flow chamber 100 in response to a measurement obtained from one or more environmental sensors 74. For example, the temperature within second compartment 30 may be adjusted to optimize detection. Additionally, the pressure in first and second compartments 10, 30 may be regulated to provide a substantially neutral pressure flow chamber 100 system.

The measured analyte concentration is dependent on the analyte production rate as well as the convective and diffusive mass transport processes occurring in the flow chamber. The flow chamber may be calibrated to account for the mass transport effects. Alternatively, it may be possible to determine the dynamic change in NO production by using mathematical modeling, such as the model described in A. A. Fadel, K. A. Barbee, D. Jaron, "A computational model of nitric oxide production and transport in a parallel plate flow chamber", Ann. Biomed Eng. 37 (2009) 943-954, which is incorporated by reference herein in its entirety. The mathematical model may be used to relate the steady-state NO concentration at the position of the electrode to the analyte production rate.

Additionally, the mathematical model may be used to determine the initial analyte production rate, which may be estimated by fitting a theoretical mathematical function to the relationship between steady-state analyte concentration changes for a range of shear stress step changes. In an exemplary embodiment, this relationship may be mathematically modeled using a simple linear model or a nonlinear relationship model, such as a hyperbolic model or sigmoidal model. The mathematical model enables the determination of steady-state analyte values at various applied shear stresses, allowing the steady state difference in the change in NO concentration between any two shear stress levels to be determined. This procedure is described in A. Andrews, D. Jaron, D. Buerk, P. Kirby and K. Barbee, "Direct, real-time measurement of shear stress-induced nitric oxide produced from endothelial cells in vitro" Nitric Oxide, 23 (2010) 335-342, incorporated by reference herein in its entirety.

The innovative flow chamber 100 offers a unique advantage by providing real-time, direct, spatial and temporal in vitro detection of analytes present in low concentrations. By insulating the analyte in a stagnant second compartment 30 separated by permeable membrane 50 from convective transport due to fluid flow in first compartment 10, fluid system 100 prevents disturbances in the fluid flow profile, prevents possible effects of the flow on analyte sensor 70, and avoids problems associated with chamber leaking at the sensor insertion site. Additionally by controlling the distance of analyte sensor 70 from the cell surface and or configuring second compartment 30 as a substantially small and enclosed space to ensure rapid equilibration and analyte and fluid in second compartment 30, accurate, and reliable quantitative concentration measurements can be obtained. Additionally, the use of the flow chamber to conduct in vitro experiments offers a significant advantage by providing the ability to control shear stress and determine analyte concentration changes in real time. This is due, in part, to the fact that the measured analyte concentrations reflect a combination of analyte production by the cells and convective and diffusive mass transport effects of the system. Experimental data may be coupled with mathematical modeling to interpret the results and to relate analyte production to shear stress.

Flow chamber 100 of the present invention may be used for variety of applications and may be particularly well suited for use as a research tool. In an exemplary embodiment, flow chamber 100 may be used to measure the amount of or changes in small cell-produced molecules, such as NO, generated in response to an applied fluid flow shear stress. In one embodiment, the flow chamber can be used to conduct and evaluate simulations in which specific signaling events are explicitly modeled. The signaling pathways can be studied in detail by simulating the effects of inhibitors or other interventions and comparing the effects on the dynamics of the NO response. Therefore the flow chamber may be used to investigate the mechanisms that determine NO production. The invention may further provide a method for studying the kinetics of the signaling mechanisms linking NO production with shear stress as well as pathological conditions involving changes in NO production or availability. Additionally, the flow chamber may be used to evaluate different theoretical models which have previously been limited by the paucity of quantitative data regarding production and transport of NO.

The device can also be used to detect and study other cell-produced diffusible molecules present in low concentrations. Alternatively, flow system 100 may be used for chemical analyte analysis that and need not involve immobilizing cells on permeable substrate 50 or generating cell-produced analytes.

EXAMPLES

Example 1

In an experimental study, direct, real-time measurement of NO concentration changes due to flow-induced shear stress stimulation of endothelial cells in vitro using the flow chamber of the present invention was investigated. The measured NO concentrations reflect a combination of NO production by the cells and convective and diffusive mass transport effects of the system. The experimental protocol set forth in the study provides a method for studying the mechanisms linking NO production with shear stress as well as pathological conditions involving changes in NO production or availability.

Bovine aortic endothelial cells (BAECs) were cultured in Dulbecco's modified Eagle's medium (Mediatech Cellgro), supplemented with 10% fetal bovine serum (Sigma), 2 mmol/l L-glutamine (Mediatech Cellgro), and penicillin-streptomycin (Mediatech Cellgro). The cells were grown to confluency and subsequently plated onto the lower surface of individual polyester Transwell® membranes (Corning Transwell Permeable Supports having a 24 mm diameter culture area with 3 µm pores). The Transwell® membranes were then placed in an incubator overnight, inverted and cultured for 1 day before conducting the experimental study. The Transwell® membranes were subsequently washed 3 three times with a solution of Dulbecco's Phosphate Buffered Saline (PBS) with calcium/magnesium (Sigma) supplemented with 70 µM L-arginine (L-arg) (Sigma) and inserted into the flow chamber.

The flow chamber included an electrode and equipment for measuring NO (TBR4100 4-channel Free Radical Analyzer and 200 µm diameter mini sensors for NO measurements ISO-NOPF). The electrodes were frequently recoated with nafion (Sigma) and re-calibrated during the experimental study to improve selectivity. The recoating process involved at least two dip/dry sessions. The electrodes were calibrated by the decomposition of a NO donor S-nitroso-N-acetyl-penicillamine (SNAP) using Cu(II). The SNAP was prepared by dissolving 5 mg EDTA and 5.0 mg+/−2.0 mg of SNAP in 250 mL HPLC grade water. The electrode was immersed in 12 mL of 0.1 M copper(II) sulfate in distilled water for about 1 to about 2 hours until the electrode stabilized. Aliquots of SNAP were sequentially added in an amount of about 10 µL, 20 µL, 40 µL, 80 µL after each signal reached a plateau. A multipoint calibration plot was created using Data-Trax software (produced by WPI). The sampling rate was 10 samples/s. The change in recorded potential was converted to corresponding molarities of NO produced by SNAP addition. The efficiency of the conversion of SNAP to NO was 0.6. Electrode sensitivity was at least about 10 pA/nM. The electrodes were tested for sensitivity to nitrite ($NO_2^-$) after the calibration procedure and sensitivity was found to be about 1.5% to about 3% per 100 mM. Sensitivity increased when the electrode sensitivity to NO had decreased significantly below 5 pA/nM. The temperature probe supplied by WPI was pre-scaled using a two-point entry of known temperatures (0.03125V=1° C., 0.625V=20° C.).

Figure 6:
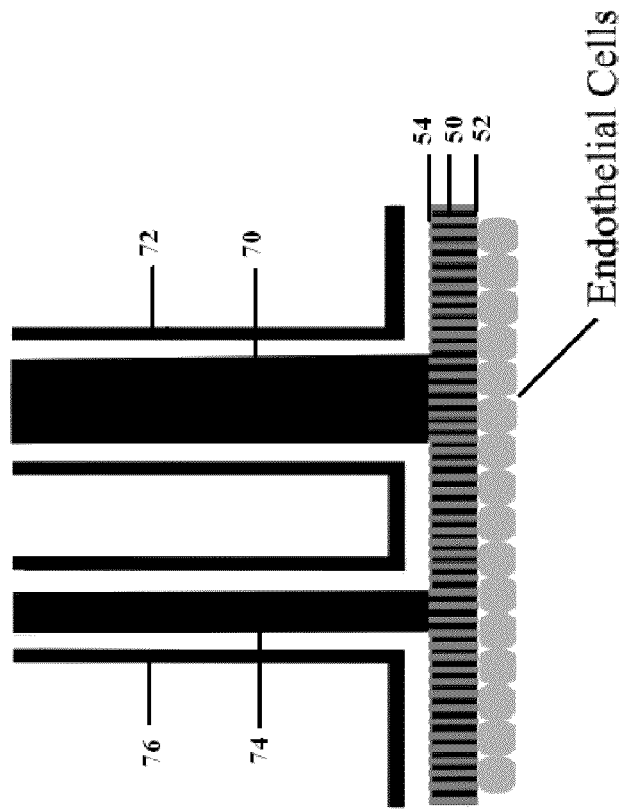
FIG. 6 is a close-up cross-sectional view of a portion of FIG. 5 showing the permeable membrane and the tips of the sensors.
Figure 5:
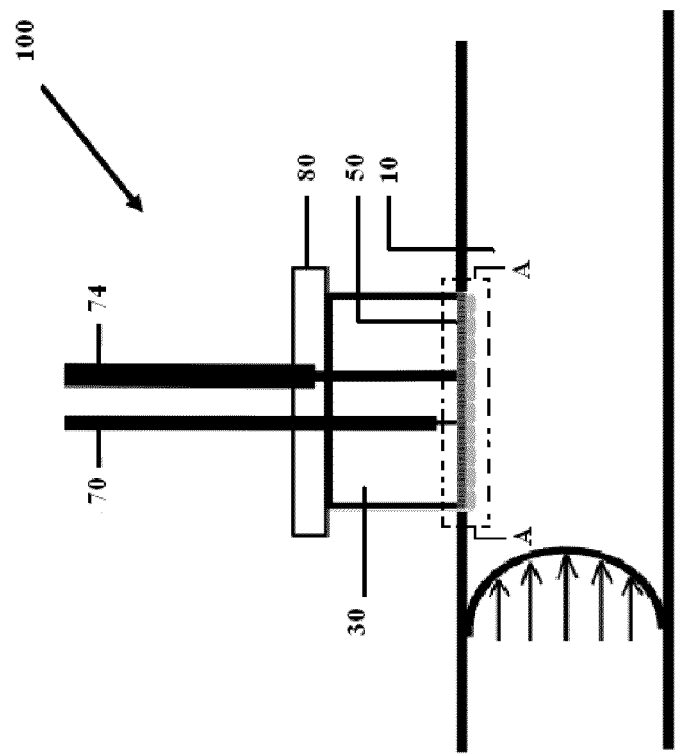
FIG. 5 is a cross-sectional view the flow chamber of FIG. 4 with the sensors present.

As shown in FIG. 4, the flow chamber was made from parallel plates of polycarbonate with a spacer that determined its height. The dimensions (in cm) of the flow channel were about: 4.57 W×12.19 L×0.025 H. The flow inlet and outlet had large reservoirs with sampling ports. A glass coverslip covered an opening in the bottom plate, allowing visualization of the cell layer and the electrode on an inverted microscope. As shown in FIGS. 5-6, endothelial cells were grown on the lower surface of a Transwell® porous membrane, which fit into the flow chamber flush with the upper plate of the flow chamber. The flow chamber had an upper compartment and lower compartment separated by the porous Transwell® membrane. Below the Transwell® membrane, fluid flowed through the parallel plate channel that defined the lower compartment, exposing the endothelial cells to uniform shear stress. Above the Transwell® membrane, a stagnant upper fluid compartment, having a small volume housed the NO electrode and temperature sensor. This design placed the electrode out of the fluid flow avoiding problems associated with potential flow sensitivities, flow disturbances and chamber leaking at the electrode insertion site. Furthermore, due to the small volume and zero flux condition at the other boundaries of the stagnant upper fluid compartment and the short diffusion distance through the membrane, the concentration of NO in the upper fluid compartment was nearly uniform and rapidly equilibrated with the concentration in the cell layer. The electrode was lowered into the upper compartment of the flow chamber until it rested on the surface of the Transwell® membrane at a fixed distance from the ECs of about 10 µm equal to the thickness of the membrane. This configuration allowed the NO generated by the cells to be measured abluminally from the endothelial cell layer. Due to the temperature sensitivity of the NO electrode, the flow chamber was enclosed in a water bath at 37° C. in order to prevent heat loss and temperature fluctuations. In addition, samples were taken during experiments from sampling ports and later analyzed for NO concentration using an NO Analyzer (Sievers NAO280i).

The flow chamber was sterilized under ultraviolet light for 20 minutes before each use. The flow chamber was flushed with each of the following: 100 mL of 70% ethanol and 100 mL of deionized water and then prepped with 75 mL of the PBS with calcium and magnesium supplemented with 70 µL-arg solution. The PBS with calcium and magnesium supplemented with 70 µM L-arg solution was pumped into the lower compartment of the flow chamber using a Reglo-Z Digital pump (Ismatec). Flow rates were calculated based on desired shear stresses using Equation 1.

$$Q=\tau w h^2/6\mu \qquad \text{Equation 1}$$

where w is the chamber width of the lower flow chamber, h is the chamber height of the lower flow chamber, µ is the viscosity, τ is the shear stress (dyn/cm$^2$) and Q is the flow rate. The pump was controlled using a LabView program, which was adapted from the manufacture's online LabView driver. Using an inverted light microscope (Nikon TE300 Eclipse) under 10× objective, the electrode was lowered using a micrometer until the electrode gently rested on the surface of the Transwell® membrane. The chamber was then placed in an enclosed heated water bath of about 37° C. for an hour without flow until the electrode and temperature in the flow chamber stabilized.

Figure 7:
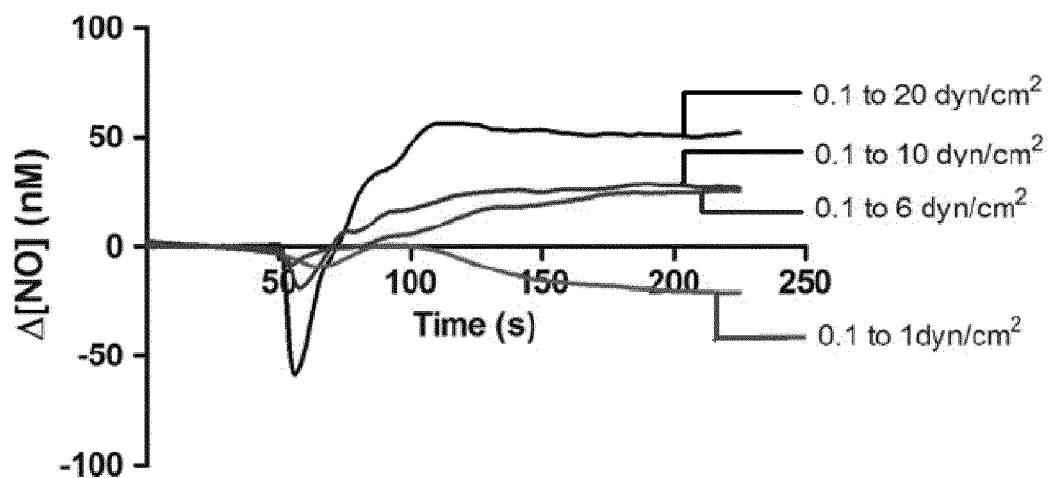
FIG. 7 is a graph of the change in NO concentration as a function of time showing shear stress-induced NO response corresponding to a change in shear stress from 0.1 dyn/cm$^2$ to 1, 6, 10 and 20 dyn/cm$^2$.

120 mL of the PBS with calcium and magnesium supplemented with 70 µM L-arg solution was cycled continuously through the lower compartment of the flow chamber during the experiment at a low flow rate of 0.25 mL/min (corresponding to a wall shear stress of 0.1 dyn/cm$^2$) to prevent the accumulation of NO due to basal (unstimulated) production. The cells plated on the Transwell® membrane were exposed to multiple step changes in flow rate ranging from about 0.1 dyn/cm$^2$ to about 20 dyn/cm$^2$ with a 3-minute interval between the step changes. Specifically, as shown in FIG. 7, a series of step changes in flow rate corresponding to shear stresses of about 1, 6, 10, and 20 dyn/cm$^2$ were applied, always returning to 0.1 dyn/cm$^2$ between stimuli.

The PBS with calcium and magnesium supplemented with 70 µM L-arg solution was then exchanged with PBS with calcium/magnesium with 1 mM Nω-Nitro-L-arginine methyl ester (L-NAME, pH 7.2, Sigma). The L-NAME solution was flushed through the lower compartment of the flow chamber. Fluid flow was subsequently turned off for 1 hour prior to repeating the same sequence of step changes that were performed prior to L-NAME treatment.

The step changes in flow elicited reproducible changes in NO concentration, wherein cells could be repeatedly stimulated without diminution of the response. The magnitudes of the responses were consistent within an experiment but varied among cultures. The chamber was continuously perfused at a low flow rate of 0.25 mL/min (corresponding to a wall shear stress of 0.1 dyn/cm$^2$) to prevent the accumulation of NO due to the basal (unstimulated) NO production. A series of step changes in flow rate corresponding to shear stresses of 1, 6, 10 or 20 dyn/cm$^2$ were applied, always returning to 0.1 dyn/cm$^2$ between stimuli. The steady-state NO concentration at 0.1 dyn/cm$^2$ was offset to zero in order to show the change in NO concentration in response to each step change in shear stress, shown to occur at 50 second intervals. The cellular response to the applied shear stress involved a sharp, transient decrease in NO concentration upon step change initiation followed by an increase in NO concentration to a new, higher steady-state.

Figure 8A:
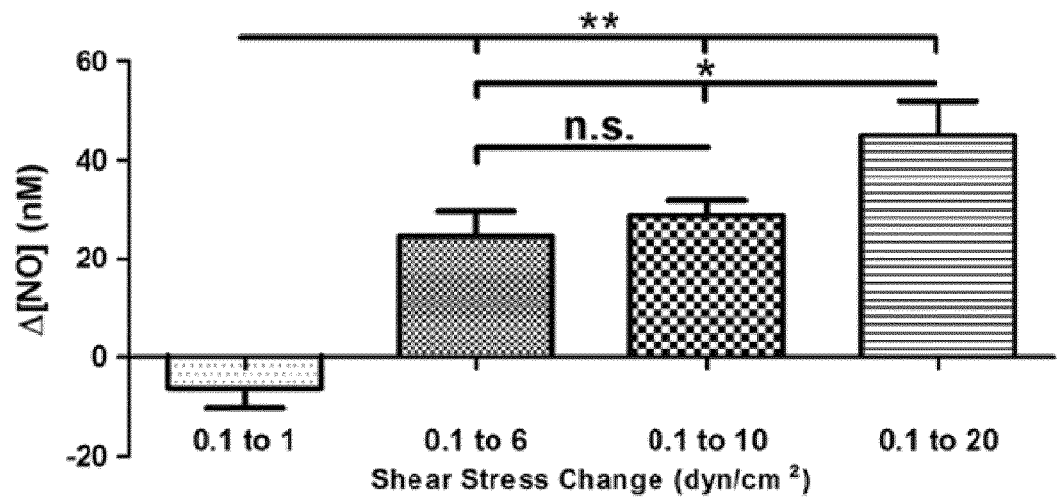
FIG. 8(a) is a graph of the change in NO concentration as a function of the shear stress change for experiments involving a change in shear stress from 0.1 dyn/cm$^2$ to 1, 6, and 20 dyn/cm$^2$.

The change in steady-state was calculated as the difference between the baseline prior to the step change and the steady-state value following the step change, as shown in FIG. 8(a). The differences were calculated using the average concentration over a 13 s interval prior to the step change and the average concentration at the new steady-state over a 9 s interval after the step change. The steady-state change averaged about −6 nM for a step change to 1 dyn/cm$^2$, about 25 nm for a step change to 6 or 10 dyn/cm$^2$ and about 45 nM for a step change to 20 dyn/cm$^2$. In addition, the magnitude of the initial decrease was found to be shear-stress dependent. For the steady-state concentration to increase with increased shear stress, the NO production rate must exceed the rate of removal by the increased convective transport effects.

The steady-state change at 20 dyn/cm² was statistically different from the change observed in response to 6 or 10 dyn/cm² but was not statistically significant between 6 and 10 dyn/cm². The steady-state change from 0.1 to 1 dyn/cm² was statistically different from step changes to all the other shear stresses. Concentration changes ranged from about −21 nM to about 9 nM, from about 19 nM to about 53 nM, from about 20 nM to about 47 nM and from about 24 nM to about 62 nM for a step change to 1, 6, 10 and 20 dyn/cm². However, because convective transport is higher at the higher flow rate, the NO production rate must have been higher at 10 dyn/cm² than at 6 dyn/cm². Additionally, the magnitude of the initial decrease in NO concentration was found to be shear-stress dependent, suggesting that the transient decrease was related to the convective effect of the step change in flow.

Figure 8B:
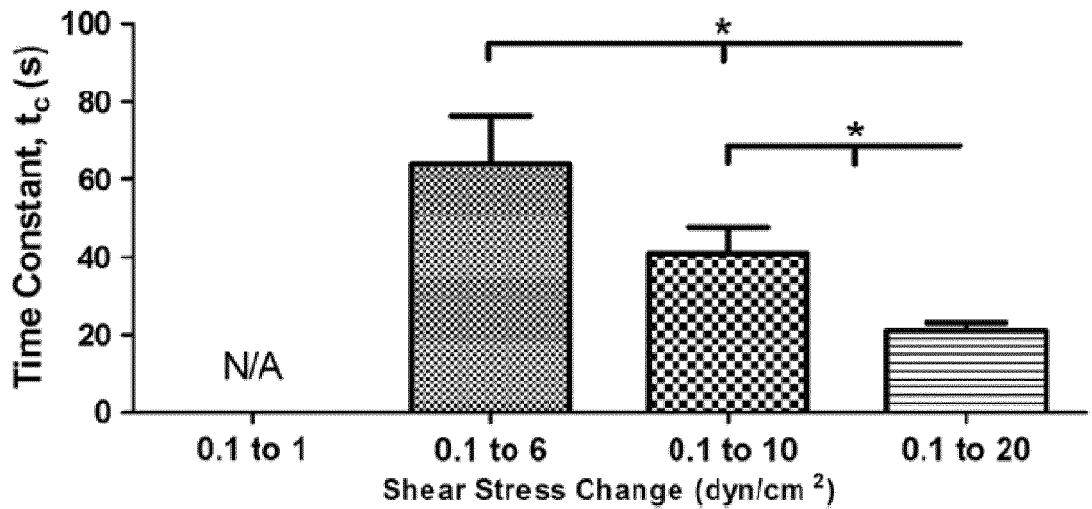
Figure 9A:
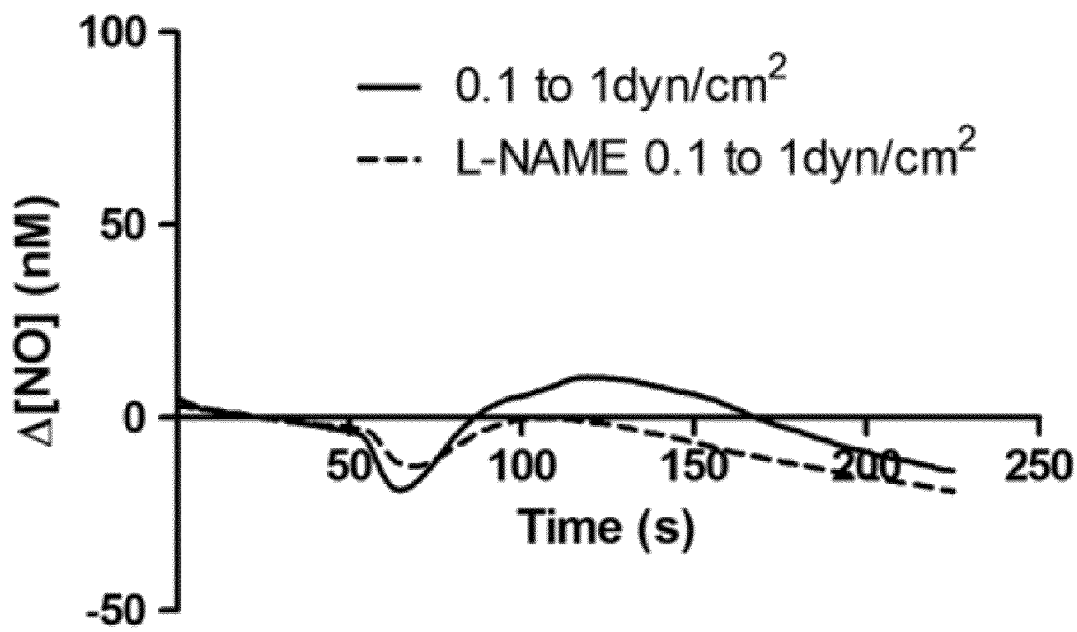
FIG. 9(a) is a graph comparing the change in NO concentration as a function of time showing shear stress-induced NO response to a step change from 0.1 to 1 dyn/cm$^2$ before and after treatment with 1 mM L-NAME.
Figure 9B:
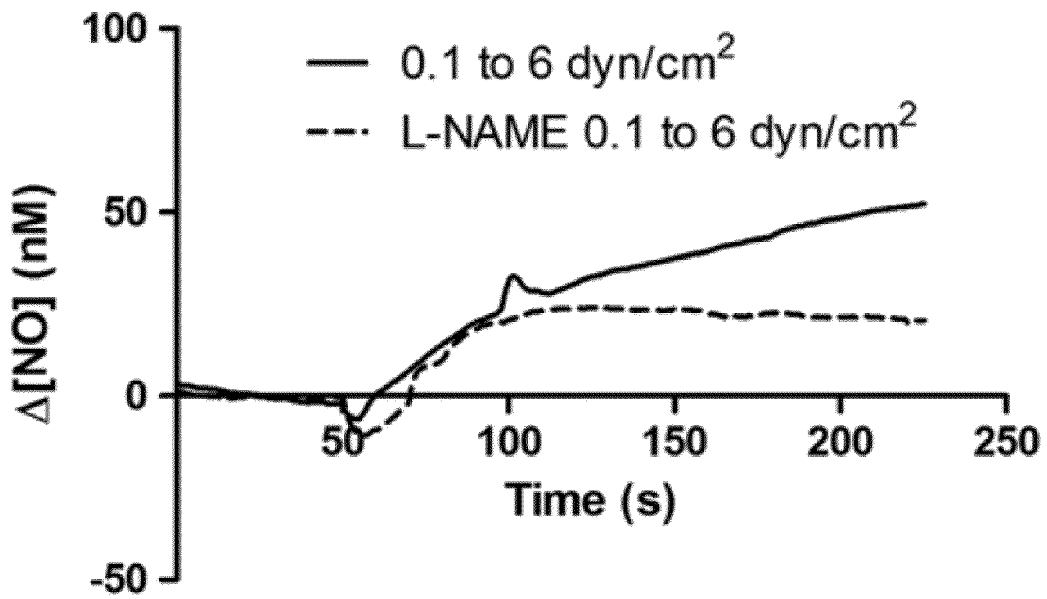
FIG. 9(b) is a graph comparing the change in NO concentration as a function of time showing shear stress-induced NO response to a step change from 0.1 to 6 dyn/cm² before and after treatment with 1 mM L-NAME.
Figure 9C:
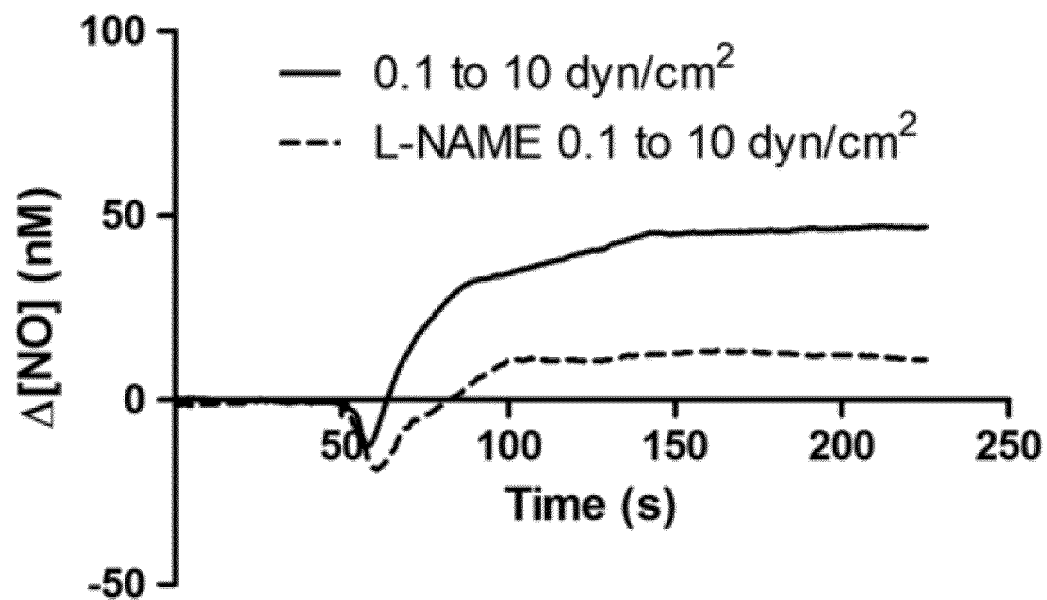
FIG. 9(c) is a graph comparing the change in NO concentration as a function of time showing shear stress-induced NO response to a step change from 0.1 to 10 dyn/cm² before and after treatment with 1 mM L-NAME.
Figure 9D:
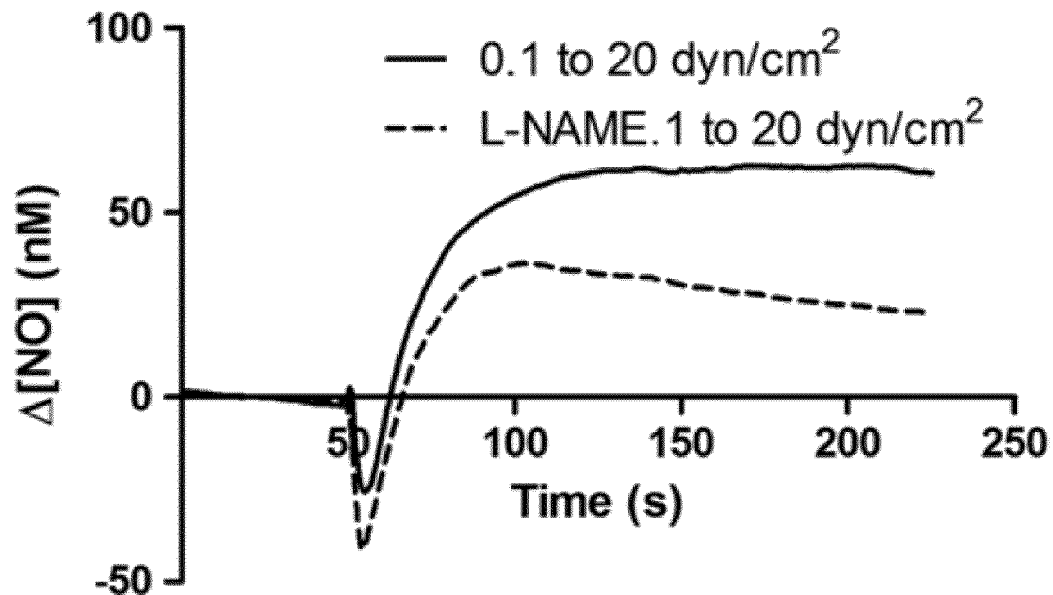
FIG. 9(d) is a graph comparing the change in NO concentrations as function of time showing shear stress-induced NO response to a step change from 0.1 to 20 dyn/cm² before and after treatment with 1 mM L-NAME.

As shown in FIG. 8($b$), the time course of the NO concentration profiles following a step change were analyzed using an exponential fit to calculate the time constant ($t_c$). Average $t_c$ values were 64 s, 41 s, and 21 s for 6, 10 and 20 dyn/cm², respectively. Exponential curves did not accurately reflect the time course for a step change from 0.1 to 1 dyn/cm². Mean and SE were plotted and statistics were calculated using the paired two-tail t-test n=8 for 1, 6 and 10 dyn/cm² and n=6 for 20 dyn/cm², p<0.05. For time constants, one value each for 6 dyn/cm² and for 10 dyn/cm² were significant outliers and were excluded using Grubb's test α=0.05. The ability to measure changes in NO concentration in real-time allowed for analysis of the kinetics of the responses of endothelial cells to changes in shear stress. The time constants characterizing the rate at which the concentration approached the steady-state decreased significantly as the size of the step change in shear stress increased. This suggests that in addition to the steady-state production rate being dependent on shear stress, the rate at which the signaling processes leading to increased production are activated is also dependent on the size of the shear stress stimulus. The simulation of the time course of NO concentration changes due to an instantaneous increase in production in response to a step in shear stress indicates that there is negligible transport lag in the measurement system. Therefore, the time dependence of the concentration changes reflects the dynamics of the cellular response.

Shear stress-induced NO responses were compared before and after L-NAME treatment. Following stimulation at multiple shear stresses, the experimental fluid was exchanged with 1 mM L-NAME having a pH of 7.2. Measurements with L-NAME were made under the same protocols as were used prior to treatment with L-NAME with the shear stress starting at 0.1 dyn/cm² and then increasing in step changes to 1, 6, 10 or 20 dyn/cm². As shown in the sample traces of FIGS. 9($a$)-9($d$), step change occurs at 50 second intervals. The steady-state concentration at 0.1 dyn/cm² was offset to zero in order to show the individual NO response due to the step change. The solid lines in these figures represent the NO response prior to L-NAME treatment and the dotted line represents the NO response after L-NAME treatment, with the exception of the range of 0.1 to 1 dyn/cm².

Figure 10:
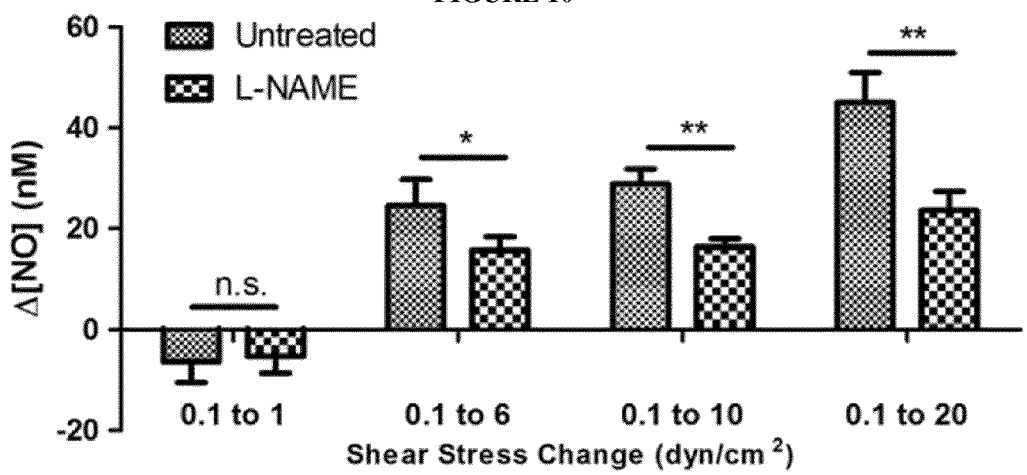
FIG. 10 is a graph of the change in NO concentration in response to shear stress step changes before and after treatment with L-NAME.

FIG. 10 shows a comparison of the steady-state NO concentration changes in response to a step change before and after treatment with L-NAME. These changes were calculated between steady-state concentrations before and after application of a step change in shear stress. Comparison of the steady-state changes between untreated and L-NAME treated responses were found to be statistically significant between step changes from 0.1 to 6, 10 and 20 dyn/cm² but not for 0.1 to 1 dyn/cm² but were not for 0.1 to 1 dyn/cm². FIG. 10 shows that steady-state changes after treatment with L-NAME were reduced by 40% and were statistically significant for all changes in shear stress, with p values of p<0.05 and p<0.01 for a paired one-tailed t-test. The mean and SE were plotted, wherein n=8 for 6 and 10 dyn/cm², n=6 for 20 dyn/cm², p<0.05; p<0.01; for paired one-tailed t-test. Steady-state changes after treatment with L-NAME averaged 60% of the untreated values. One value for 6 dyn/cm² was a significant outlier and was excluded using Grubb's test α=0.01. The concentration changes were attenuated by the endothelial nitric oxide synthase (eNOS) inhibitor L-NAME, confirming the validity of the flow chamber technique for NO measurement. A decrease in the baseline concentration following treatment with L-NAME was observed but was not reflected in the data because the measurements only examine relative changes in NO concentration. Thus, the effects of L-NAME treatment on the absolute concentrations of NO were more profound than suggested by the 40% reduction of the shear stress response.

The measured NO concentration is dependent on the production rate of NO as well as the convective and diffusive mass transport processes occurring in the flow chamber. To account for the transport effects in the flow chamber and consequently, properly interpret the measured concentration changes, the transport process was mathematical modeled to determine the dynamic changes in NO production. The experimental results were compared to a mathematical model of transient and steady-state NO transport. A. A. Fadel, K. A. Barbee, D. Jaron, "A computational model of nitric oxide production and transport in a parallel plate flow chamber", *Ann. Biomed Eng.* 37 (2009) 943-954, describes the development of the mathematical model. Within the flow domain (described by plane Poiseuille flow), the convection-diffusion equations for the transport of NO were solved using finite element analysis. Production of NO occurred in the 5 um thick endothelial layer where mass transport is by diffusion only. An auto-oxidation reaction was included in both domains with the oxygen concentration taken to be a constant throughout the chamber. The dimensions and configurations of the chamber in the mathematical computations accounted for a membrane of about 10 μm and the stagnant compartment above the cell layer.

Figure 11:
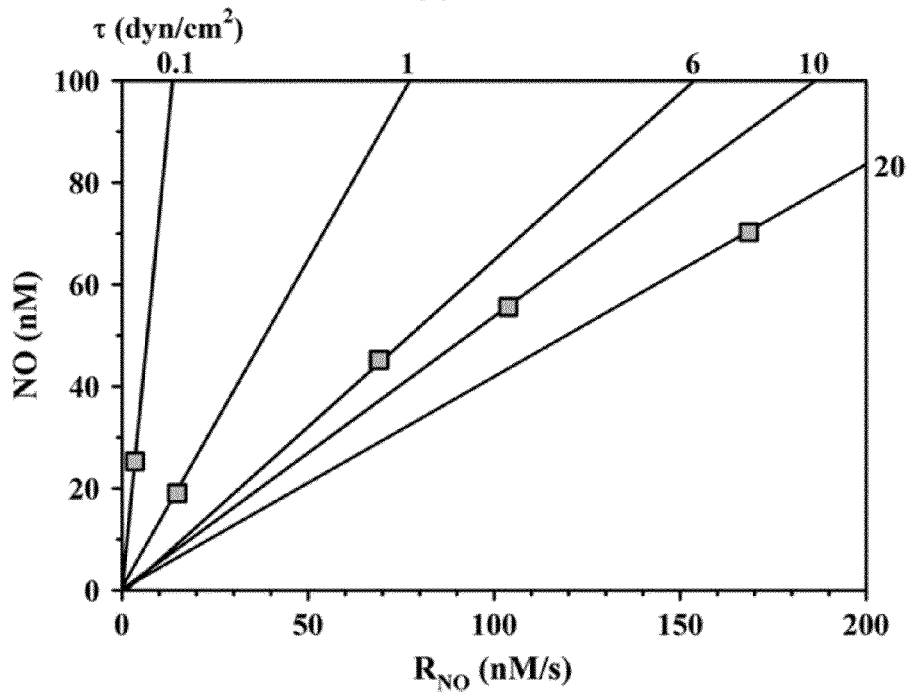
FIG. 11 is a graph of steady-state NO concentration as a function of the rate of production of NO.

The model permitted relation of the steady-state NO concentration at the position of the electrode to the production rate within the endothelial layer. This relationship was approximately linear with the slope strongly dependent of the shear rate, as shown in FIG. 11. The solid lines of FIG. 11 represent the relationship of steady-state NO concentration as a function of $R_{NO}$ for each of the shear stress values used in the study. These relationships demonstrated that the size of a stimulated change in production rate, represented by the measured change in NO concentration depends on the baseline concentration.

Although the measurement technique used in this experiment only determined the relative changes in NO concentration, using the computational model for the flow chamber, it was possible to estimate the basal production rate of NO based on an analysis of the steady-state concentration changes for a range of shear stress step changes. If the baseline concentration at 0.1 dyn/cm² is known or can be estimated, then the measured change in NO concentration can be related to the change in production rate. By fitting an expression for the shear-stress dependent production of NO to the measured changes in NO concentration in response to a range of shear stress steps, the basal production rate was estimated. Three relationships for shear-stress dependent $R_{NO}$ were investigated to determine the best fit for the steady-state experimental results for each relationship, as shown in FIGS. 12(a)-12(b).

The simplest model tested for NO production rate was linear with shear stress ($R_{NO}=R_{basal}+A\tau$; black bars), where $R_{basal}$ is the basal production rate, $R_{NO}$ is the rate of NO production, A is the slope and $\tau$ is shear stress. Two nonlinear relationships for $R_{NO}$ as a function of shear stress were also investigated: a hyperbolic model ($R_{NO}=R_{basal}+R_{sat}\tau/(\tau+A)$; represented in FIG. 12(a) by the bar with horizontal hatching, where $R_{sat}$ is the maximum rate of stimulated production (above $R_{basal}$), and a sigmoidal model ($R_{NO}=R_{max}/(1+A\exp^{-B\tau})$; hatched bars), where $R_{max}$ is the maximum rate of production. The basal rate for the sigmoidal model can be calculated from $R_{basal}=R_{max}/(1+A)$. Predicted steady-state NO values at each shear stress for each relationship were obtained from the computational model for the flow chamber, allowing the steady-state difference in the change in NO concentration between any two shear stress levels to be determined.

Figure 12A:
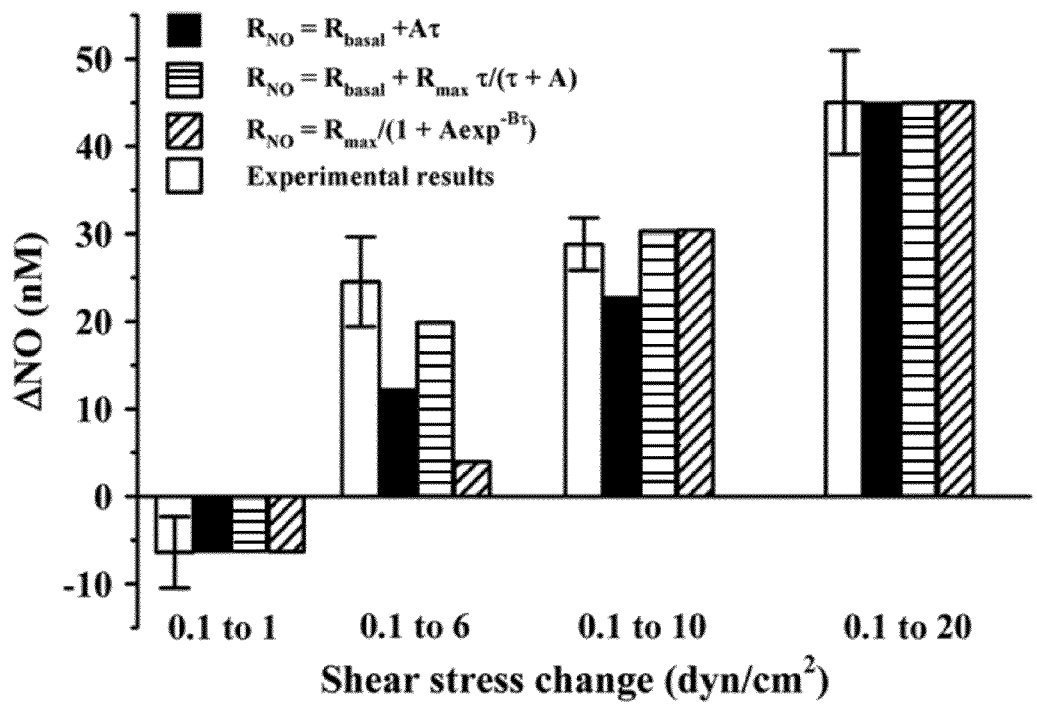
FIG. 12(a) is a graph comparing the experimental results for changes in shear stress (open bars, mean±SE) with steady-state change in NO concentration predicted from 3 different models for shear stress-dependent rate of NO production ($R_{NO}(\tau)$: linear=black bars, hyperbolic=bars with horizontal hatching, sigmoidal=bars with diagonal hatching).
Figure 12B:
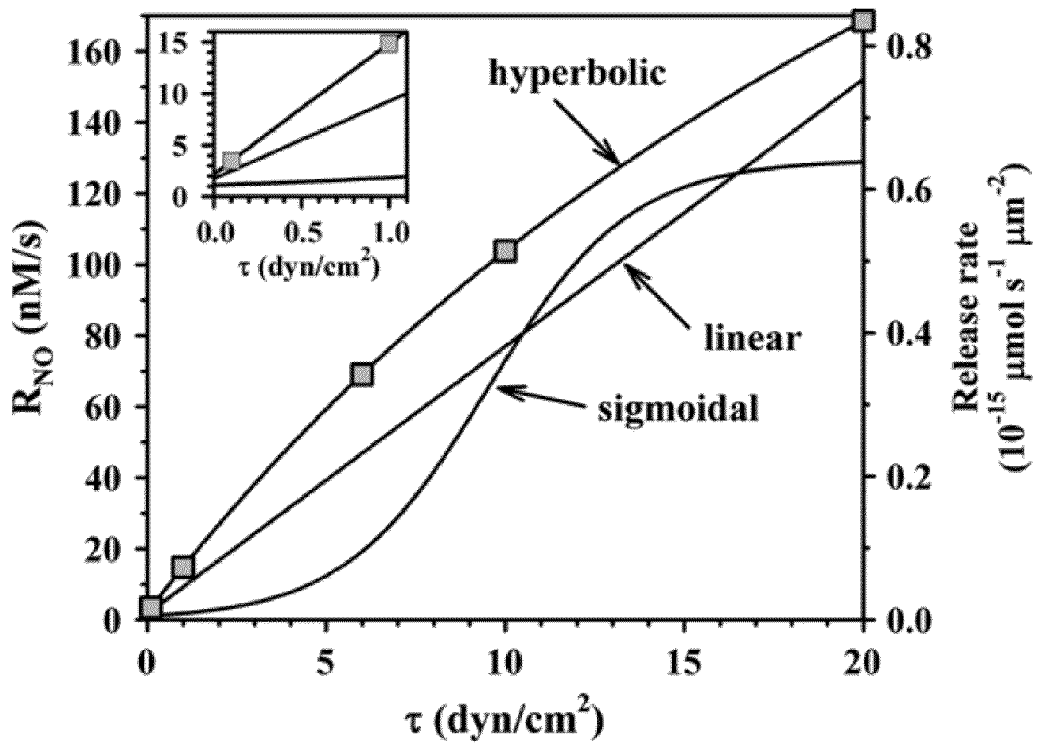
FIG. 12(b) is a graph showing NO production rates and corresponding NO release rates as a function of shear stress (r) with best-fit parameters for each model.

Comparisons for the best fit of these models to the experimental data (mean±SE, open bars) are shown in FIG. 12(a). The linear model (represented by the black bar) provided the least suitable fit. The two nonlinear models appear to provide excellent fits to most of the experimental data, although both underestimate the change in NO for the change in shear stress from 0.1 to 6 dyn/cm². The hyperbolic model (represented by the bar with horizontal hatching) provided the closest match to the data. Although the sigmoidal function could be made to fit the discrete data points fairly well, the production rate was nearly constant within the plateau phase of the curve while shear stress (and thus convective transport) increased. This would lead to a non-physiological situation in which NO concentration decreases at shear stress values higher than a local maximum occurring between 10 and 20 dyn/cm². Calculated values for the basal NO production rate ($R_{basal}$) at zero shear stress and $R_{NO}$ at different shear rates based on parameters that provided the best fit to the to the experimental data for each relationship are summarized in Table 1 and shown graphically in FIG. 12(b). In FIG. 12(b), the calculated $R_{NO}$ and release rates for experimental shear stresses are shown for the hyperbolic model at $\tau=1$ dyn/cm².

TABLE 1

Analysis of experimental results from flow chamber using different models of shear-stress dependent NO production.

| | $\tau$ (dyn/cm²) = | | | | | |
|---|---|---|---|---|---|---|
| | 0 | 0.1 | 1 | 6 | 10 | 20 |
| Model | $R_{basal}$ | $R_{NO}(\tau)$ | (nM/s) | | | |
| $R_{NO} = R_{basal} + A\tau$ | 1.74 | 2.49 | 9.26 | 48.9 | 76.9 | 152 |
| $R_{NO} = R_{basal} + R_{max}\tau/(\tau + A)$ | 2.13 | 3.43 | 14.8 | 69.1 | 104 | 168 |
| $R_{NO} = R_{max}/(1 + A\exp^{-B\tau})$ | 1.12 | 1.17 | 1.83 | 19.3 | 73.0 | 129 |

Model parameters.
Linear, A = 7.52 (nM/s)/(dyn/cm²).
Hyperbolic, $R_{max}$ = 457.5 nM/s, A = 35 dyn/cm².
Sigmoidal, $R_{max}$ = 129.5 nM/s, A = 115, B = 0.5 cm²/dyn.

The three models for shear stress-dependent $R_{NO}$ were also fit to steady-state NO concentration change data that was obtained from the L-NAME studies. The hyperbolic model provided the best fit, and the linear model the least suitable fit. All the models underestimated the experimental data for the 0.1 to 1 dyn/cm² change in shear stress. The analysis found that L-NAME partially inhibited $R_{NO}$ under the experimental condition of the study (L-arg also in perfusate). At the highest shear stress change (0.1 to 20 dyn/cm²), $R_{NO}$ was about 57.3%, about 57.6%, and about 58.3% of $R_{NO}$ estimated from untreated ECs using the linear, hyperbolic and sigmoidal models, respectively.

Figure 13:
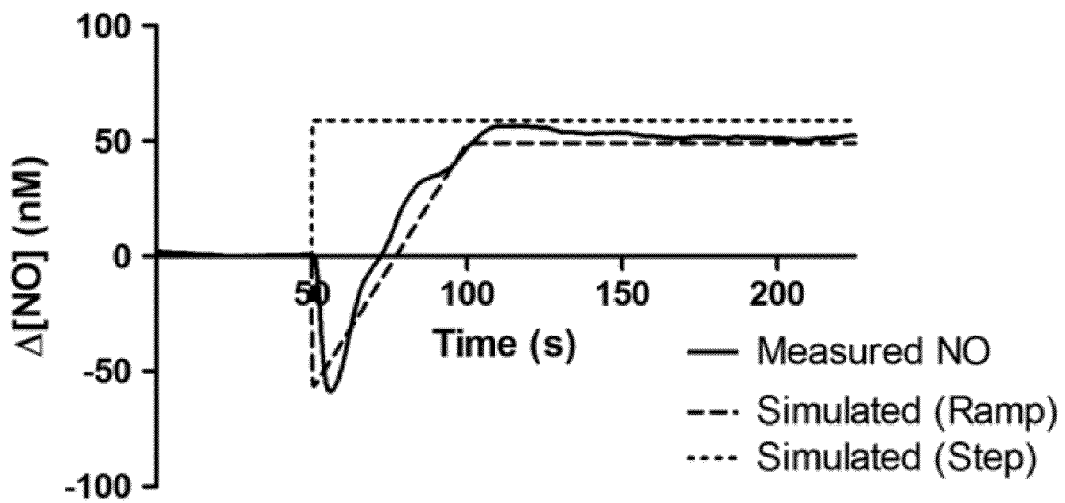
FIG. 13 is a graph showing a comparison of the experimental results and mathematical simulations.

The computer models also permitted investigation of the role of mass transport in the dynamics of the transient response. As shown in FIG. 13, simulations of NO concentrations were evaluated at the electrode location for a step change in shear stress from about 0.1 dyn/cm² to about 20 dyn/cm². The initial decrease in NO concentration was followed by an increase to an elevated steady-state concentration. Two mathematical simulations are shown in FIG. 13 utilizing either a time-dependent (ramp) (dashed line) or time independent (instantaneous step) relationship (dotted line) between NO production and shear stress. Simulations were performed for a shear stress change from 0.1 to 20 dyn/cm², which occurred at 50 s. The time-independent model demonstrated that following a step change a steady-state concentration was reached almost instantaneously. The time-dependent model utilized a linearly increasing production rate in response to the initiation of shear stress. This produced an initial decrease in NO concentration in response to the change followed by an increase until a new steady-state concentration was reached. The model describes NO production as a basal production rate plus a shear stress-dependent NO production component. In one simulation, the stimulated production rate of NO was dependent on shear stress alone, with no lag between change in shear stress and the increase in production rate. In this case, the NO concentration reached its new steady-state almost instantaneously. In contrast, when a gradual increase in production rate linear with time was simulated, it was possible to mimic the time-dependent changes in NO concentration observed experimentally, including the transient decrease and subsequent slower rise to the new steady-state. The nearly instantaneous response to a step change in production indicates that the response time of the NO measurement is not limited by diffusion through the membrane. The time course of the NO concentration changes therefore reflects a time-dependent cellular response rather than a transport lag.

The experiment enabled direct, real-time measurement of NO concentration changes due to flow-induced shear stress stimulation of endothelial cells in vitro. The concentration changes were partially attenuated by the endothelial nitric oxide synthase (eNOS) inhibitor L-NAME. The failure of L-NAME to completely abolish the NO response may in part be due to the incomplete removal of L-arg from the upper compartment. However, the level of inhibition that was observed is consistent with previous studies with L-NAME treatment of in vivo vessels.

The experimental results indicated that following a step change from a low shear stress of 0.1 dyn/cm² to higher shear stresses, the NO concentration at the electrode first transiently decreased and then increased to a steady-state concentration that is higher than the initial steady-state value except for a shear stress change to 1 dyn/cm². As suggested by the experimental simulations, this initial decrease is due to convective washout whose effect is immediate. Since the simulated production rate is actually the net release of NO from the cell (production minus any consumption by the cell), in this experiment, changes in NO due to NO production were indistinguishable from changes in NO due to reactions consuming NO within the cell. Thus, the possibility that the lag in release was due in part to increased production accompanied by a simultaneous increase in NO consumption through rapid reactions with reactive species such as superoxide or lipid peroxyl radicals could not be ruled out. When an instantaneous increase in production rate was simulated, it was predicted that a very rapid increase in NO concentration with no transient decrease would be observed. In addition, the magnitude of the initial decrease in the experimental results was found to be shear-stress dependent, supporting the idea that the transient decrease was related to the convective effect of the step change in flow.

Following the initial decrease, the concentration increased to a new steady-state that was higher than the pre-stimulus level. The ability to measure changes in NO concentration in real-time allows analysis of the kinetics of the responses of endothelial cells to changes in shear stress. The time constants characterizing the rate at which the concentration approached the steady-state decreased significantly as the size of the step change in shear stress increased. This suggested that in addition to the steady-state production rate being dependent on shear stress, the rate at which the signaling process leading to increased production are activated was also dependent on the size of the shear stress stimulus. The simulation of the time course of NO concentration changes due to an instantaneous increase in production in response to a step in shear stress indicated that there was negligible transport lag in our measurement system. Therefore, the time dependence of the concentration changes reflected the dynamics of the cellular response.

For the steady-state concentration to increase with increased shear stress, the stimulated NO production rate must exceed the rate of removal by the increased convective transport effects. The experimental data and analysis showed that for small increase in shear stress, the concentration deceased despite an increase in production rate. This was consistent with previous study predictions. Furthermore, even though the steady-state concentration changes for 6 and 10 dyn/cm² were similar, the changes in production rate at 10 dyn/cm² were much greater than at 6 dyn/cm², as shown in Table 1 and FIG. 12(*b*).

The relationships between steady-state NO concentration and production rate for different flow conditions presented in FIG. 11, provided a template for interpreting the measured responses in terms of stimulated changes in production. Use of this template required knowledge of the absolute concentration in the baseline condition. This could be determined through the development of an in situ calibration procedure. Alternatively, as accomplished in the present experiment, the basal production rate was estimated by fitting a theoretical relationship between production rate and shear stress to the measured NO changes for a range of shear stress step changes. In the study, as shown in Table 1, the highest value for $R_{NO}$ occurred at $\tau=20$ dyn/cm². The technique of the present experiment permitted observation of the dynamics of the $R_{NO}$ response on a small time scale. The experimental measurements combined with mathematical modeling of the transport processes also enabled determination of the dynamic changes in NO production by the cells.

Example 2

Direct, real-time measurement of NO concentration changes due to flow-induced shear stress stimulation of endothelial cells in vitro using the flow chamber of the present invention was performed. In this study, solutions of Dulbecco's Phosphate Buffered Saline (PBS) with calcium/magnesium (Sigma), supplemented with 70 μM L-arginine (L-arg) (Sigma) or 1 mM L-NAME solution (Sigma) were tested using the flow chamber in the same manner as described in Example 1, with the exception that the NO was measured in response to step changes in flow rate corresponding to shear stresses from about 1 dyn/cm² to about 5 dyn/cm² and from about 1 dyn/cm² to about 10 dyn/cm², the same experimental protocol as that of Example 1 was utilized.

The step change from about 1 to about 5 dyn/cm² produced an increase in NO that is approximately 70% of the response to 10 dyn/cm². Endothelial cells exposed to shear stress in the presence of 1 mM No methyl ester (L-NAME) significantly reduced the flow induce NO response, consistent with its action as a competitive inhibitor of NO synthase.

It is to be understood that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

The invention claimed is:
1. A flow chamber for detecting an analyte comprising:
a first compartment, wherein said first compartment comprises:
a fluid inlet and a fluid outlet for allowing a fluid to flow through said first compartment;
a second compartment;
a first analyte sensor positioned within said second compartment for detecting an analyte produced by cells located in said first compartment;
a permeable membrane, wherein said permeable membrane comprises:
a first surface that is exposed to fluid flow in said first compartment; and
a second surface in said second compartment,
wherein said permeable membrane separates said first compartment from said second compartment, and said permeable membrane has a pore size in a range of from about 0.1 μm to about 12 μm and a porosity of no more than 0.14;
and a flow rate controller for controlling flow of a fluid between said fluid inlet and said fluid outlet in said first compartment in a direction substantially parallel to a surface of said permeable membrane, said flow rate controller being configured to cycle said fluid flow rate between a control flow rate and a plurality or different higher flow rates each of the higher flow rates exerting a different shear stress on the surface of the membrane in said first compartment.
2. The flow chamber of claim 1, wherein said first analyte sensor is positioned at a known predetermined distance from said first surface of said membrane.
3. The flow chamber of claim 2, wherein said predetermined distance is about 5 μm to about 50 μm.
4. The flow chamber of claim 1, wherein a distal end of said first analyte sensor contacts said second surface of said membrane.
5. The flow chamber of claim 1, wherein said second compartment comprises a fluid inlet and a fluid outlet to permit rinsing of said second compartment with a fluid.
6. The flow chamber of claim 1, wherein said first analyte sensor is adapted to detect a small molecule selected from the group consisting of: dissolved gases, ions, sugars, nucleotides, proteins and lipids.
7. The flow chamber of claim 1, further comprising a second analyte sensor positioned within said first compartment, wherein said first and second analyte sensors are adapted to detect different analytes.

8. The flow chamber of claim 1, further comprising a sensor holder associated said second compartment and said first analyte sensor for positioning said first analyte sensor in said second compartment.

9. The flow chamber of claim 1, wherein said second compartment is a substantially enclosed internal space having a volume less than about 1 mL.

10. The flow chamber of claim 1, wherein the exerted shear stresses exerted by the fluid flow rate is within a range of 0 to about 200 dyn/cm$^2$.

11. The flow chamber of claim 1, wherein the exerted shear stresses correspond to a series of step changes in the flow rate.

12. The flow chamber of claim 11, wherein the series of step changes in flow rate correspond to shear stresses within the range of 1 to 20 dyn/cm$^2$.

13. A method for detecting an analyte using a flow chamber comprising:
    positioning a plurality of cells within the flow chamber of claim 1 on said first surface of the permeable membrane;
    flowing a fluid through said first compartment; and
    detecting, in said first compartment, one more analytes produced by said plurality of cells.

14. The method of claim 13, wherein said permeable membrane allows for passage of said analyte and wherein said analyte is produced by said plurality of cells.

15. The flow chamber of claim 13, wherein the exerted shear stresses exerted by the fluid flow rate is within a range of 0 to about 200 dyn/cm$^2$.

16. The flow chamber of claim 13, wherein the exerted shear stresses correspond to a series of step changes in the flow rate.

17. The flow chamber of claim 13, wherein the series of step changes in flow rate correspond to shear stresses within the range of 1 to 20 dyn/cm$^2$.

18. A flow chamber for detecting an analyte comprising:
    a first compartment, wherein said first compartment comprises:
        a fluid inlet and fluid outlet for allowing a fluid to flow through said first compartment;
    a second compartment;
    an analyte sensor positioned within said second compartment for detecting an analyte produced by cells located in said first compartment; and
    a permeable membrane for allowing passage of an analyte from said first compartment to said second compartment,
    wherein said analyte sensor is positioned at a known distance from a surface of said permeable membrane, and said permeable membrane has a pore size in a range of from about 0.1 µm to about 12 µm and a porosity no more than 0.14;
    and a flow rate controller for controlling flow of a fluid between said fluid inlet and said fluid outlet in said first compartment in a direction substantially parallel to a surface of said permeable membrane, said flow rate controller being configured to cycle said fluid flow rate between a control flow rate and a plurality of different higher flow rates each of the higher flow rates exerting a different shear stress on the surface of the membrane in said first compartment.

19. The flow chamber of claim 18, wherein first analyte sensor is removably fixed in place by a fastener.

20. The flow chamber of claim 18, wherein said predetermined distance is about 5 µm to about 50 µm.

* * * * *